United States Patent [19]

Slover et al.

[11] 4,445,235

[45] May 1, 1984

[54] STOOL SPECIMEN COLLECTOR

[76] Inventors: Pearl Slover, 345 Sybil Ave., San Leandro, Calif. 94577; Robert R. Moore, 1897 National Ave., Hayward, Calif. 94545

[21] Appl. No.: 417,197

[22] Filed: Sep. 13, 1982

[51] Int. Cl.³ .............................................. A47K 11/00
[52] U.S. Cl. ...................... 4/144.2; 4/144.1; 4/451; 4/455
[58] Field of Search ...................... 4/661, 144.1, 144.2, 4/301, 450, 451, 452, 455

[56] References Cited

U.S. PATENT DOCUMENTS

| | | | |
|---|---|---|---|
| 2,840,826 | 7/1958 | Ebbesen et al. | 4/661 |
| 3,381,315 | 5/1968 | Glassberg | 4/144.2 X |
| 3,704,142 | 11/1972 | Wilson | 4/144.1 |
| 3,754,287 | 8/1973 | Taylor | 4/661 |
| 3,775,777 | 12/1973 | Roberts, Jr. | 4/144.2 |
| 3,990,119 | 11/1976 | Barrett | 4/144.1 |
| 4,203,169 | 5/1980 | Dale | 4/144.2 X |
| 4,309,782 | 1/1982 | Paulin | 4/144.2 X |

Primary Examiner—Henry K. Artis
Attorney, Agent, or Firm—Bielen & Peterson

[57] ABSTRACT

A stool specimen collector for collecting a medical patient's feces for laboratory examination and test, the collector having a subtantially impervious receptacle with a pair of side straps having an adhesive surface portion for contact adhesion to the top surface of a conventional toilet seat, the container being suspended below the toilet seat and above the surface of the toilet water, positioned to catch and retain a fecal specimen.

3 Claims, 4 Drawing Figures

U.S. Patent  May 1, 1984  4,445,235
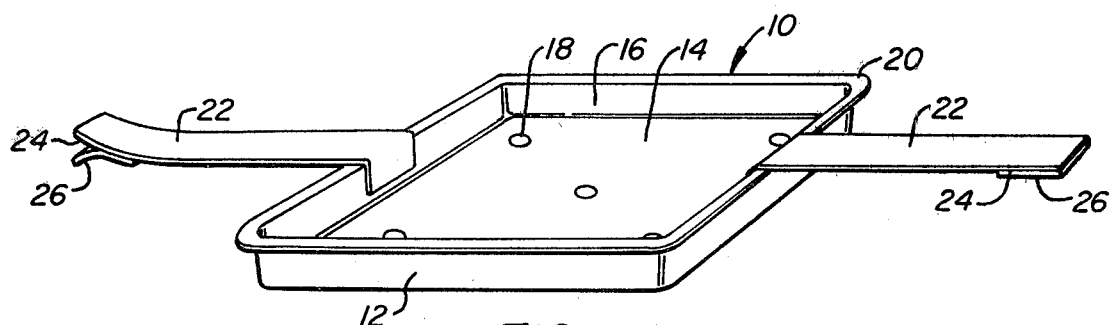
FIG._1.
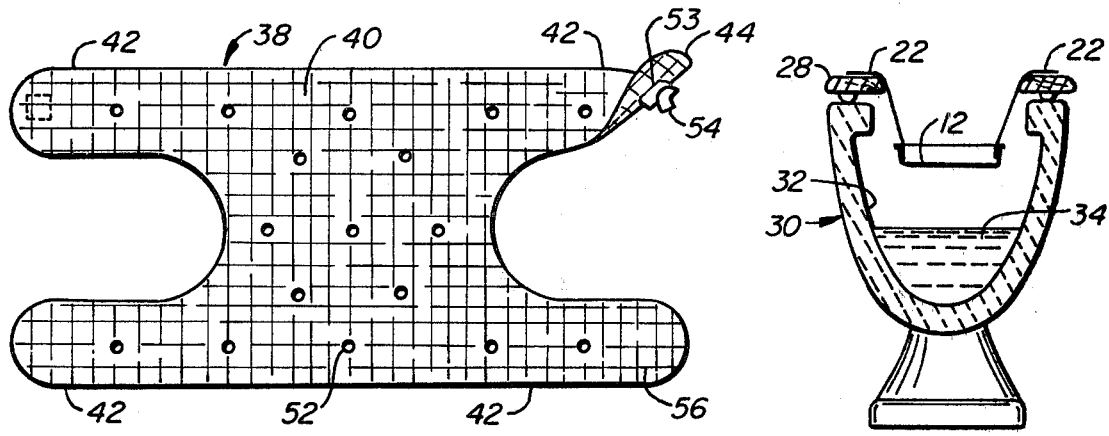
FIG._3.
FIG._2.
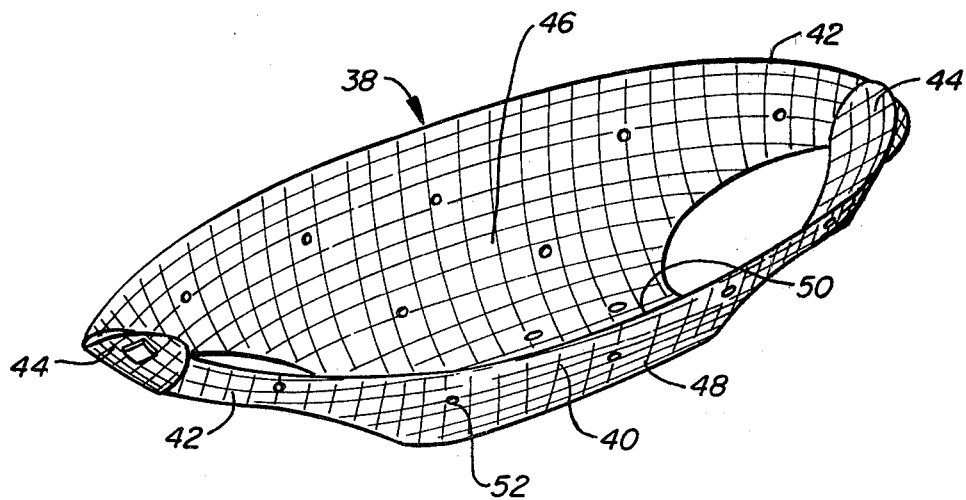
FIG._4.

STOOL SPECIMEN COLLECTOR

BACKGROUND OF THE INVENTION

This invention relates to a collector device for collection of a medical patient's stool specimen for examination and testing by a physician or a medical test laboratory. For many illnesses, particularly stomach and intestinal tract disorders, it is a conventional and common practice to examine and test a patient's feces for diagnostic and treatment purposes. Also, some post-operative monitoring procedures include periodic examination of the patient's feces.

Stool specimen collection has in the past been accomplished by the patient, with or without assistance, holding a pan or other container under the rectum, either in a squatting position or while sitting on a conventional toilet. The awkward nature of such procedures is evident. Specimens have also been collected by retrieving the specimen from the toilet water with a scoop after a patient has defecated. This method has the potential of contaminating the specimen with unclean toilet water, which may in some occasions adversely affect a test or analysis.

The past methods of stool collection are not only awkward to perform, but are somewhat embarrassing to the patient. Further, such methods commonly use a container that is not self draining, causing added problems of spillage, and subsequent separation for analysis, or that is not disposable, causing problems of possible contamination.

The stool specimen collection device of this invention is constructed for convenient attachment to a conventional toilet seat with a receptacle centrally located below the seat, above the water level in the toilet. The collection device is fabricated from a material that is water resistant, or at least not structurally denegrated by water or fluid discharge by the patient. The device is preferably constructed with a receptacle that includes perforations to allow drainage of liquids that may otherwise be inadvertently entrapped in the receptacle. The drainage feature facilitates removal of the collector from attachment to the seat, and placement of the collector and contents into a sealable container for transport to the examination facility.

The collector device of this invention is designed primarily for the convenience of the users, allowing the patient to defecate in a normal comfortable manner using a conventional flush toilet, and allowing the patient or medical staff to remove and package the specimen quickly, conveniently and without contaminating auxiliary components such as pans, trays or the like. The relief of the patient's tension and anxiety alone allows the stool sample procedure to be accomplished with minimum delay and complication. The simplicity of the procedure allows for office out-patient or home use of the device for collection of the necessary specimens.

SUMMARY OF THE INVENTION

The stool specimen collector of this invention comprises a receptacle and an integral attachment means for suspending the receptacle below the seat of a conventional toilet and above the level of the toilet water. The receptacle is designed to catch and retain a patient's feces during the normal process of defecating. The collector is fabricated from materials that are water resistant or that have a wet strength, and that can be easily disposed. Preferably, the material is biodegradable or combustible without toxic fumes.

The design of the receptacle is preferably such that inadvertent passage of urine onto the collector will be drained through the receptacle for convenient handling of the collector during removal and transport for examination. This feature is most effectively accomplished by the inclusion of a plurality of small drainage holes in the receptacle of the collector. To maximize the retention of the patient's stool specimen in the receptacle particularly where the collected specimen may be of a loose or wet consistency and would pass through a net-type receptacle design, the holes are relatively small and uniformly spaced over the surface area of the receptacle.

The attachment means of the collector is constructed of strap members fixed to, or integral with, the receptacle. The strap members preferably include adhesive segments to directly adhere the strap members to the surface of the toilet seat or to the surface of the top rim of the toilet bowl. While the strap members could include or comprise thin laces to tie the suspended receptacle to the seat, the method of adhesive attachment is preferred for the convenience of attachment of the collector to the toilet apparatus and removal therefrom.

These and other features of the stool specimen collector are described in greater detail in the description of the preferred embodiments hereafter.

BRIEF DESCRIPTION OF THE DRAWINGS

FIG. 1 is a perspective view of one embodiment of the stool specimen collector.

FIG. 2 is a side elevational view of the collector of FIG. 1 placed in position on a conventional toilet, illustrated in partial cross-section.

FIG. 3 is a top plan view of an alternate embodiment of a specimen collector, before assembled into a preferred configuration for placement in use.

FIG. 4 is a top plan view of the alternate embodiment of the collector placed in position for use on a conventional toilet.

DESCRIPTION OF THE PREFERRED EMBODIMENTS

Referring to FIG. 1, a first embodiment of the stool specimen collector is shown and designated generally by the reference numeral 10. The specimen collector is constructed with a shallow open receptacle 12 having a bottom 14 and peripheral sides 16 forming a tray-like structure. The receptacle 12 has a plurality of drain holes 18 through which fluid, received in the collector, can conveniently pass.

The receptacle 12 is preferably fabricated from a rigid or semi-rigid material that is water resistant or maintains its structural integrity when wet.

The wet strength requirement is necessary to prevent the weight of a wet stool specimen from splitting an untreated receptacle made, for example, of paper.

The receptacle may also become inadvertently wet from contact with the toilet water or upon passage of urine by the patient and must retain its strength when receiving the specimen.

The tray-like structure of the receptacle 12 shown in FIGS. 1 and 2 is constructed from a P.V.A. plastic that is eventually dissolvable in water but which will maintain a structural integrity, even when wet, for the expected period of use as a specimen collector. Alternately, the receptacle can be constructed from a cardboard material treated for water resistance, which also permits biodegradability after expected duration of use.

While other plastic materials may be employed, it is desired that they at least be combustible or heat degradable without toxic emission as disposal of the semi-rigid collector may likely be accomplished by burning in a hospital furnace.

The sides 16, bottom 14 and a top rim 20 of the receptacle 12 are integrally fabricated in a stamping process. The drain holes 18 are punched in the bottom 14 of the receptacle, and are sufficiently large for drainage of inadvertently passed urine, without loss of the fecal specimen through the holes.

Connected by an adhesive to two opposed sides of the collector are elongated straps 22. The straps 22 are fabricated from a flexible treated paper and have a non-curing adhesive section 24 on the underside of the distal ends of the straps which, prior to use, are protected by peel-off backing strips 26.

As illustrated in FIG. 2, when the backing strip is removed, the adhesive ends of the straps 22 can be pressed against the top of a seat 28 of a conventional toilet 30. The length of the straps are such that the receptacle 12 is centered within the bowl 32 of the toilet 30 below the seat and above the level of the toilet water 34.

The patient simply defecates in a normal manner, preferably using restraint on discharge of urine. The feces is caught by the receptacle before falling to the water. There should be no added discomfort from sitting on the strap ends that adhere to the seat, particularly with an additional protective paper seat cover, as is common in most lavatories. The straps may, if desired, be adhered directly to the rim 36 of the toilet without affecting the positioning of the receptacle by proper adjustment of the straps 22.

The collector is sized to be adequate for central positioning within the bowl with a maximum likelihood of catching the patient's discharge, yet allowing by-pass of a urinal discharge and toilet disposal of toilet paper. Conveniently, the size of the receptacle is one quarter to one half the diameter of the bowl at the level where the receptacle is located.

Where expense and convenience of disposability are important factors, a one piece paper collector is preferred. Referring to FIG. 3, a flat pattern for a paper stool specimen collector, designated generally by the reference numeral 38, is shown. The paper collector 38 has a central portion 40 with four projecting integral strap elements 42, with two parallel elements projecting as a pair from each opposite side of the central portion.

As shown in FIG. 4, the pairs of strap elements have distal ends 44 that are overlapped and secured together by an adhesive. The resultant structure, when supported by the opposed, mutually overlapped ends 44, deforms the central portion into an open cradle receptacle 46 having a depressed center 48 and a raised periphery 50.

To provide adequate drainage of water and other liquids, the flat pattern has a plurality of perforations or holes 52 punched through the paper material before interconnection of the distal ends. Although the distal ends may be connected by the user, it is preferred that they be connected during the manufacturing process to avoid confusion on arranging the strap elements on the toilet seat.

The two pairs of interconnected strap elements each have an adhesive pad 53 with a peel-off strip 54 adhered to one side of the overlapped ends. In a similar manner to the previously described embodiment, the backing strip 54 is removed and the strap pairs adhered to the top surface of the seat of a conventional toilet.

The paper collector is fabricated from a flexible water-resistant paper with an internal fibre reinforcement web 56. The material, composition and size of the collector pattern allows the entire collector and any remaining stool specimen to be disposed by flushing down the toilet. The water resistance of the material is such that it eventually deteriorates, allowing the collector to freely pass through conventional waste water systems. The collector and specimen may be placed in a plastic or water resistant paper bag (not shown) for temporary storage or transport, after the specimen has been collected. The described features make the paper collector compact for storage in a folded condition, easy to use by the average patient, and convenient to dispose.

While on the foregoing embodiments of the present invention have been set forth in considerable detail for the purposes of making a complete disclosure of the invention, it may be apparent to those of skill in the art that numerous changes may be made in such detail without departing from the spirit and principles of the invention.

What is claimed is:

1. A stool specimen collector for use by a medical patient for collection of a stool specimen comprising:
    a flat, flexible water-resistant material having a perforated central portion with four projecting, integral strap elements with two shaped parallel elements projecting in a pair from each opposite side of said central portion, said strap elements having distal ends with attachment means for attaching the strap elements to a toilet, wherein on use of said collector, said distal ends in each pair are connected and attached to opposite sides of the top of a conventional toilet, said central portion forming an open cradle receptacle with a depressed center and raised periphery, said receptacle being supported below the seat of the toilet, above the bowl water for receiving the feces of a user and wherein said center portion and said four projecting integral strap elements are formed from a one piece pattern.

2. The stool specimen collector of claim 1 wherein said one piece pattern is fabricated from a paper material.

3. The stool specimen collector of claim 2 wherein said distal ends in each pair are preconnected and include adhesion means for adhering the preconnected ends to the toilet.

* * * * *